US00PP22241P3

(12) United States Plant Patent
Lock

(10) Patent No.: US PP22,241 P3
(45) Date of Patent: Nov. 8, 2011

(54) ***HAWORTHIA* PLANT NAMED 'L1'**

(50) Latin Name: *Haworthia limifolia*
Varietal Denomination: L1

(75) Inventor: Peter Lock, Krimpen a/d Ijssel (NL)

(73) Assignee: Wander Tuinier BV

( * ) Notice: Subject to any disclaimer, the term of this patent is extended or adjusted under 35 U.S.C. 154(b) by 27 days.

(21) Appl. No.: 12/460,358

(22) Filed: Jul. 18, 2009

(65) Prior Publication Data

US 2011/0016594 P1 Jan. 20, 2011

(51) Int. Cl.
*A01H 5/00* (2006.01)

(52) U.S. Cl. ..... Plt./373

(58) Field of Classification Search ..... Plt./373
See application file for complete search history.

(56) References Cited

OTHER PUBLICATIONS

GTITM UPOVROM Citation for 'L1' as per QZ PBR 20080798; Apr. 14, 2008.*

* cited by examiner

*Primary Examiner* — Kent L Bell

(57) ABSTRACT

A new and distinct *Haworthia* cultivar named 'L1' is disclosed, characterized by a single rosette of foliage, and distinctive horizontal white bands on green foliage. The new variety is a *Haworthia*, typically produced as a garden or container plant.

1 Drawing Sheet

Figure 1:
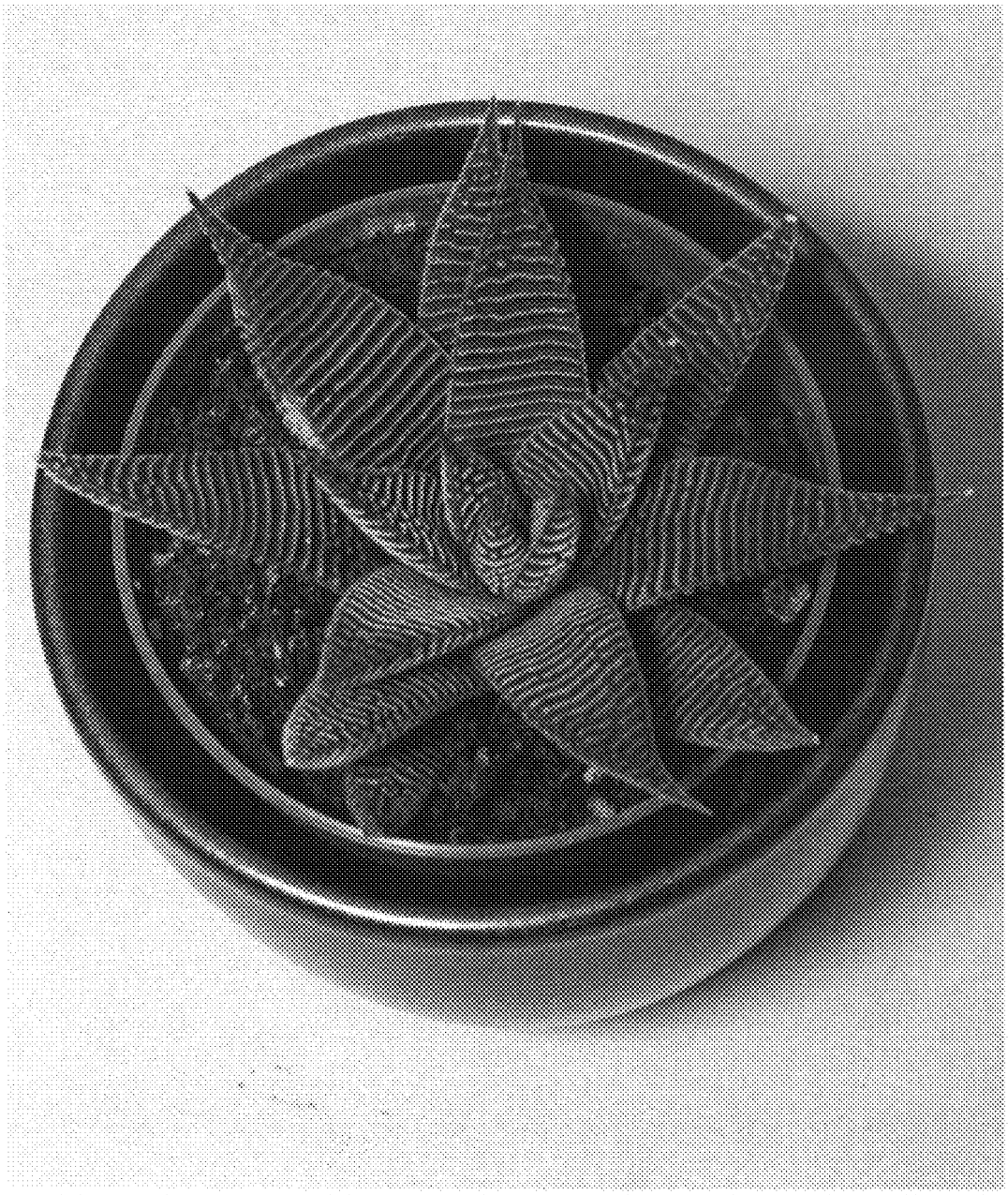

Latin name of the genus and species: *Haworthia limifolia.*
Variety denomination: 'L1'.

BACKGROUND OF THE INVENTION

The new cultivar was discovered as a chance, naturally occurring, whole plant mutation of the parent variety, an unnamed variety of *Haworthia limifolia*. 'L1' was discovered by Peter Lock, a citizen of the Netherlands in a commercial planting of *Haworthia limifolia* in November of 2003, at a commercial greenhouse in s'Gravenzande, The Netherlands.

Asexual reproduction of the new cultivar 'L1' was first performed in the Netherlands, at a commercial laboratory by tissue culture in May 2006. 'L1' has since produced several generations and has shown that the unique features of this cultivar are stable and reproduced true to type.

SUMMARY OF THE INVENTION

The cultivar 'L1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'L1.' These characteristics in combination distinguish 'L1' as a new and distinct *Haworthia* cultivar:

1. Unique white bands crossing the entire leaf surface.
2. Foliage occurs in a single rosette, with no off-sets observed.

PARENTAL COMPARISON

Plants of the new cultivar 'L1' are similar to plants of the parent variety, an unnamed variety of *Haworthia limifolia* in most horticultural characteristics. However, plants of the new cultivar 'L1' produce foliage with a green horizontal stripe, whereas the parent variety has entirely green leaves.

The parent variety is also the best commercial comparison to the new variety.

BRIEF DESCRIPTION OF THE PHOTOGRAPH

The accompanying photograph in FIG. 1 illustrates in full color a typical plant of 'L1' indoors in the Netherlands. This plant is approximately 10 months old, shown in a 4 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The, R.H.S. Colour Chart, 2001, except where general terms of ordinary dictionary significance are used. The following observations and measurements describe 'L1' plants in a commercial greenhouse in Kimpen aan de Issel, the Netherlads. Temperatures ranged from 12° C. to 15° C. night and day. No artificial light, photoperiodic treatments or chemical treatments were given to the plants. Measurements and numerical values represent averages of typical plant types.
Botanical classification: *Haworthia limifolia* 'L1 .'
Age of the plant described: Approximately 10 months.

PROPAGATION

Time to initiate roots: Approximately 20 to 25 days at 21° C.
Root description: Fibrous
Propagation method: Tissue culture.

PLANT

Growth habit: Compact, rosulate succulent.
Container size: 4 inch.

Height: Approximately 3.5 cm.

Plant spread: Approximately 9.3 cm.

Growth rate: Slow, approximately 4 cm per year.

Branching characteristics: Non-branching, no stems or lateral branches. To date, only a single basal rosette of leaves has been observed.

FOLIAGE

Leaf:

*Arrangement.*—Rosulate, simple leaf.

*Average quantity of leaves per rosette.*—18.

*Average length.*—Approximately 4.6 cm.

*Widest width.*—Approximately 1.8 cm.

*Height/thickness.*—Approximately 0.6 cm.

*Shape of blade.*—Subulate.

*Apex.*—Narrow acute.

*Base.*—Broad cuneate.

*Margin.*—Entire.

*Texture of top surface.*—Rough, dull, non-pubescent.

*Texture of bottom surface.*—Rough, dull, non-pubescent.

*Color.*—Young foliage upper side: Near RHS Green N137A, base Greyed-Orange 177B. Horizontal stripes near White N155C. Stripes average a distance of 0.15 cm apart from each other, with an average width of 0.05 cm. Average number of stripes of 23 per leaf. Young foliage under side: Near RHS Green 137B, base Greyed-Orange 177B. Horizontal stripes near White N155C. Stripes average a distance of 0.15 cm apart from each other, with an average width of 0.05 cm. Average number of stripes of 23 per leaf. Mature foliage upper side: Near RHS Green N137A, base Greyed-Orange 177B. Horizontal stripes near White N155C. Stripes average a distance of 0.15 cm apart from each other, with an average width of 0.05 cm. Average number of stripes of 23 per leaf. Mature foliage under side: Near RHS Green 137B, base Greyed-Orange 177B. Horizontal stripes near White N155C. Stripes average a distance of 0.15 cm apart from each other, with an average width of 0.05 cm. Average number of stripes of 23 per leaf.

*Venation.*—Venation not visible.

*Petiole.*—No petiole.

Other characteristics: Foliage highly resistant to tearing or breaking due to mechanical stress. No stipules, tendrils, thorns, or spines present.

FLOWER

Bud production and flower production has not been observed to date.

REPRODUCTIVE ORGANS

Not observed due to lack of flower production.

OTHER CHARACTERISTICS

Disease resistance: Neither resistance nor susceptibility to diseases or pests has been observed in this variety.

Drought tolerance and temperature tolerance: Drought tolerant succulent. Low temperature tolerance is unknown. Tolerates high temperature to at least 45° C.

Fruit/seed production: Fruits and seeds have not been observed to date.

What is claimed is:

1. A new and distinct cultivar of *Haworthia* plant named 'L1' as herein illustrated and described.

* * * * *